United States Patent [19]

Davis, Jr.

[11] Patent Number: 4,543,821
[45] Date of Patent: Oct. 1, 1985

[54] METHOD AND APPARATUS FOR MEASURING RELATIVE PERMEABILITY AND WATER SATURATION OF A CORE

[75] Inventor: Lorne A. Davis, Jr., Houston, Tex.

[73] Assignee: Texaco Inc., White Plains, N.Y.

[21] Appl. No.: 561,499

[22] Filed: Dec. 14, 1983

[51] Int. Cl.⁴ ............................................. E21B 49/02
[52] U.S. Cl. ......................................... 73/153; 73/38; 324/376
[58] Field of Search .......................... 73/153, 38, 64.3; 436/5, 31; 324/376

[56] References Cited

U.S. PATENT DOCUMENTS

| | | | |
|---|---|---|---|
| 2,165,214 | 7/1939 | Blau et al. | 324/58.5 A X |
| 2,963,641 | 12/1960 | Nanz | 324/376 |
| 4,274,283 | 6/1981 | Maus et al. | 73/153 |
| 4,304,122 | 12/1981 | Tentor | 73/153 X |

*Primary Examiner*—Jerry W. Myracle
*Attorney, Agent, or Firm*—Robert A. Kulason; Ronald G. Gillespie

[57] ABSTRACT

A method of determining the oil and water relative permeabilities and the water saturation of a core of earthen material which includes providing two types of liquids to the core in a manner so that the liquids mix to form a two phase liquid which moves through the core. The core is irradiated with microwave energy while the liquid is in the core. A received energy signal is generated in accordance with the microwave energy that has passed through the core. A liquid pressure drop along a predetermined length of the core is sensed and a representative pressure drop signal is provided. The oil and water relative permeabilities and the water saturation of the core are derived in accordance with the flow rate of the liquid, the received energy signal and the pressure drop signal. The liquid flow rate may be either sensed or the liquid may be provided at a predetermined flow rate.

14 Claims, 4 Drawing Figures

4,543,821

METHOD AND APPARATUS FOR MEASURING RELATIVE PERMEABILITY AND WATER SATURATION OF A CORE

BACKGROUND OF THE INVENTION

Field of the Invention

The present invention relates to meters and monitors measuring characteristics of a core of an earthen material and, more particularly, to meters and monitors measuring the oil and water relative permeabilities and the water saturation of a core of earthen material.

SUMMARY OF THE INVENTION

A method of determining the oil and water relative permeabilities and water saturation of a core of earthen material for a two phase liquid includes providing two types of liquid in a manner that the liquids mix to form a two phase liquid which moves through said core. The core is irradiated with microwave energy while the liquid is flowing through it. A received energy signal is generated in accordance with the microwave energy that has passed through the core. A liquid pressure drop along a predetermined length of said core is sensed and a representative pressure drop signal is provided. The relative oil and water permeabilities and the water saturation of the core is derived in accordance with the flow rate of the liquid, the energy signal and the pressure drop signal. The flow rates of the liquids are predetermined.

The objects and advantages of the invention will appear more fully hereinafter, from a consideration of the detailed description which follows, taken together with the accompanying drawings, wherein one embodiment is illustrated by way of example. It is to be expressly understood, however, that the drawings are for illustrative purposes only, and are not to be construed as defining the limits of the invention.

DESCRIPTION OF THE INVENTION

In the analyses of a petroleum reservoir in an earth formation, one analysis relates to the oil and water relative permeabilities of the reservoir's formation to water saturation of the reservoir's formation. The conventional method of measuring the relative permeabilities to water saturation of a petroleum reservoir in an earth formation involves taking a relatively large size core from the formation and then applying what is known as a steady state relative permeability test. This method depends upon flowing a two phase liquid through the core until a steady state is achieved. The core is removed from the apparatus and weighed after each new steady state is achieved. However, the weight of the core includes the weight of the rock plus the surrounding holder (plastic, epoxy, etc.) and the liquids. The saturations are determined by the small weight differences due to the density difference between oil and water. This difference is enhanced by using a light oil and heavy water with a lot of salt in it. Not only is this method subject to error because of the small weight difference due to the density difference while measuring heavier weighted objects, but also that each removal of the core increases the chance for liquid drainage and the introduction of air into the core.

The present invention increases substantially the accuracy while speeding up the time of testing and further improves upon the testing by being able to utilize the same type of crude oil that is present in the reservoir and the same density of brine that would be used in the reservoir. Further, the conventional steady state relative permeability method can only be used at room temperature because of the disassembling process while the present invention can be used at temperatures more in keeping with the reservoir temperature.

Figure 1:
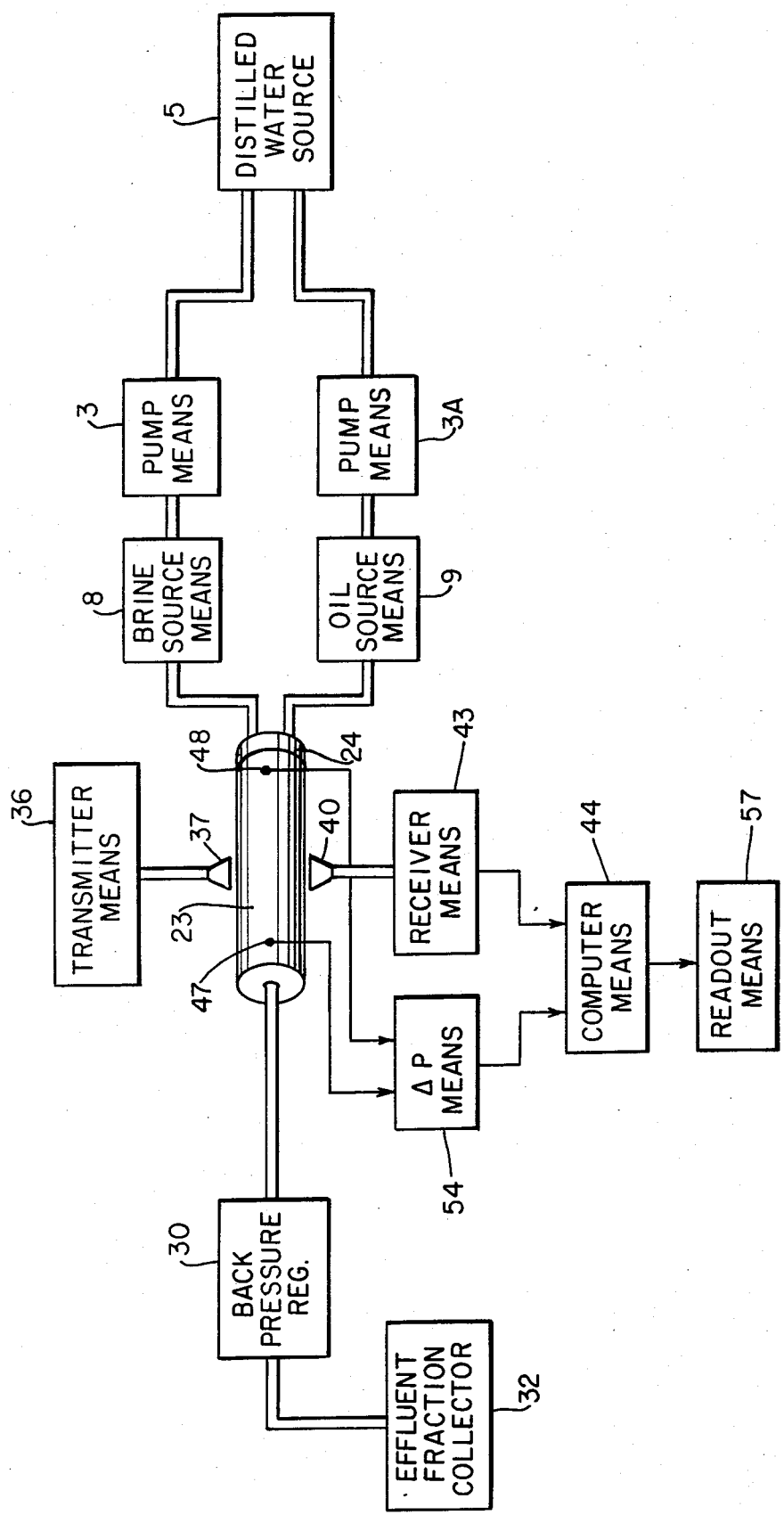
FIG. 1 is a simplified block diagram of apparatus, constructed in accordance with the present invention, for measuring the oil and water relative permeabilities and the water saturation of a core of earthen material.

Referring now to FIG. 1, pump means 3 and 3A pumps distilled water from a distilled water source 5, to provide the distilled water to brine source means 8 and to oil source means 9, respectively. The volume flow rates of pump means 3 and 3A may be controlled. Brine source means 8 and oil source means 9 each includes a conventional type free floating piston (not shown) in a container (not shown) having brine or crude oil. The pumped in distilled water causes the piston expel the brine from brine source means 8 and the crude oil from oil source means 9 to a test cell 23 includes mixing means 24 and a core 25 (shown in FIG. 2) of the earthen material from the petroleum reservoir in question.

Mixing means 24 will be explained in detail hereinafter. For the present it is sufficient to say that mixing means 24 in cooperation with test cell 23 and core 25 creates a two phase liquid which is forced through core 25.

The liquid flow through test cell 23 is provided to an optional piece of apparatus namely backpressure regulator 30. The effluent passes through backpressure regulator 30 and is provided to an effluent fraction collector 32.

While the two phase liquid is flowing through test cell 23, transmitter means 36 provides electromagnetic energy at a microwave frequency; said electromagnetic energy hereinafter shall be referred to as microwave energy. The microwave energy from transmitter means 36 is provided to an antenna 37 which radiates the microwave energy through test cell 23, and hence through core 25 within. The microwave energy that is passed through core 25 is received by an antenna 40 which provides the received microwave energy to receiver means 43. Receiver means 43 provides an electrical signal to computer means 44 in accordance with the received microwave energy. Pressure sensors 47, 48 are affixed to test cell 23 spaced a predetermined distance apart, in such a manner so as to sense the pressures at those locations on the surface of core 25 and provides corresponding signals to differentiaal pressure means 54. Differential pressure means 54 in turn provides a signal to computer means 44 corresponding to the pressure drop across the predetermined distance of core 25. Computer means 44 provides an output signal corresponding to the relative permeabilities and the water saturation of core 25 for the two phase liquid passing through it to readout means 57 in accordance with the signal from receiver means 43 and the signal from differential pressure means 54.

Figure 2:
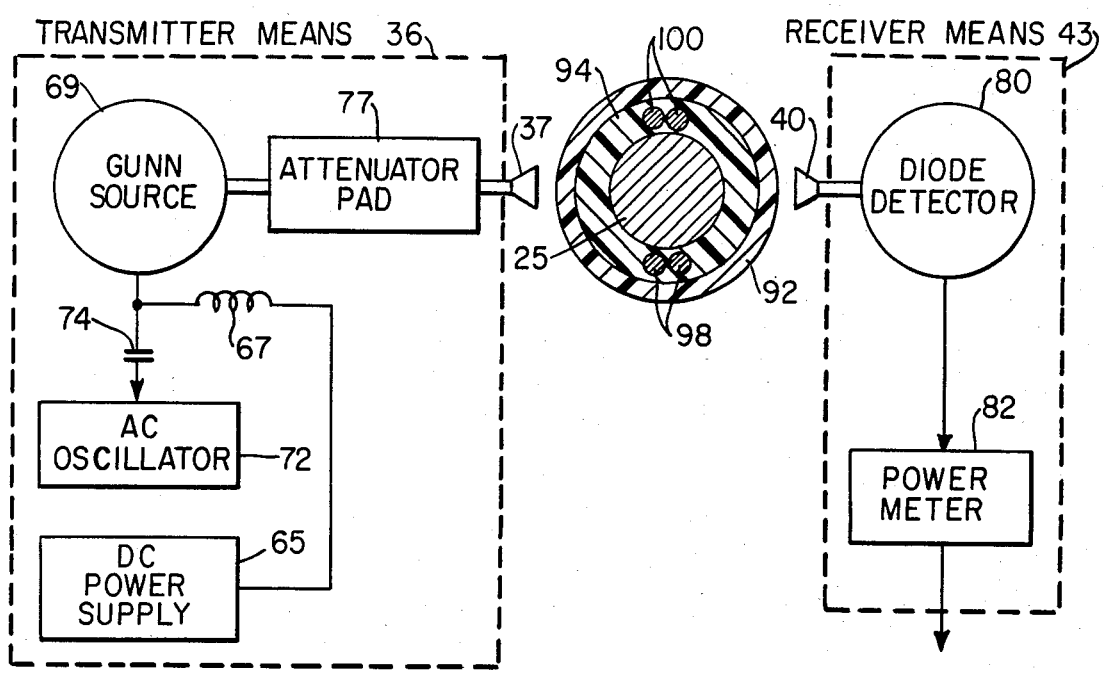
FIG. 2 is a detailed diagram of the transmitter means, the receiver means, and the test cell shown in FIG. 1.

Referring now to FIG. 2, transmitter means 36 includes a direct current power supply 65 which provides DC power through a coil 67 to a Gunn microwave source 69 of the type that is manufactured by Racon, Inc. as their part number 10014-102-02. An oscillator 72 provides an AC voltage as a predetermined frequency through a capacitor 74 to Gunn source 69. A preferred frequency of the AC voltage is 1 KHz. Gunn source 69 provides the microwave energy, at a preferred frequency of 10.525 GHz, whose amplitude oscillates at the 1 KHz frequency. Source 69 provides the microwave energy to an attenuator pad 77 which provides the microwave energy in turn to horn antenna 37. It should be noted that a horn antenna is used because the Gunn source 69 is being operated in an X-band mode. It may be desired to operate Gunn source 69 at a preferred frequency of 24.125 GHz, which is in the K-band mode and makes monitoring more independent of temperature and salinity in regards to the liquid in test cell 23. The determination of whether to use X-band or K-band is also in part determined by the core size selected. A preferred power outut for the X-band is 10 mw while for the K-band is anything greater than 50 mw to safe operating levels. Horn antenna 37 is replaced by a dielectric rod antenna and Gunn source 69 is of a type similar to that manufactured by Plessey Optoelectronics and Microwave Ltd., as their part GD0131 when operating in a K-band mode. Further, oscillator 72 may be omitted in K-band operations.

The microwave energy passing through sample cell 23 is received by another horn antenna 40 in X-band mode, or a dielectric rod antenna in the K-band mode, and provided to a diode detector 80 in receiver means 43. Diode detector 80 provides an electrical signal, corresponding to the detected microwave energy, to a power meter 82 which in turn provides the output signal to computer means 44.

Test cell 23 includes a cylindrical core 25 of an earth formation, having a preferred diameter in the range of from a ½ inch to ¾ inch and a preferred length of approximately 4 inches, and is maintained in a hard plastic tubular shell 92 by epoxy 94. Shell 92 may be made of a machineable hard plastic such as chlorinatedpolyvinylchloride or polyvinylidinedifluoride. Embedded in epoxy 94 are microwave absorber rods 98 and 100. In one particular application there are four such microwave absorber rods. One pair of absorber rods 98 is located along side of core 25 while another pair of absorber rods 100 is located diametrically opposite along side of core 25. It should be noted that core 25 is preferably oriented with relation to antennas 37 and 40 in a manner so that a straight line from antenna 37 to antenna 40 is substantially perpendicular to an axis passing through both pairs of absorber rods 98, 100. Absorber rods 98, 100 prevents the microwave energy from circumventing core 25 and being detected by diode detector 80 so as not to cause erroneous readings and so that the microwave energy detected by detector 80 is the microwave energy that has passed through core 25. Microwave absorber rods 98, 100 are made of ferrite loaded epoxy. Preferred attenuation coefficient for such material is 46 dB/cm at 10 GHz.

Referring to Figure A mixing means 24 is in actuality an end cap for test cell 23. Obviously there is another end cap at the opposite end of test cell 23 having a single exit. Since the last mentioned cap is of a conventional nature it need not be further discussed as it is not necessary to an understanding of the present invention. Mixing means 24 is made of machineable hard plastic such as chlorinatedpolyvinylchloride or polyvinylidinedifluoride having male thread 60 for mating with test cell 23. Mixing means 24 has two entrance ports 63 and 65 specifically designed to accept conventional type fittings for fluid flow. Entrance port 63 is connected to a channel 70 which permits the conducting of the liquid entering entrance port 63 to surface 72 of mixing means 24.

Figure 3A:
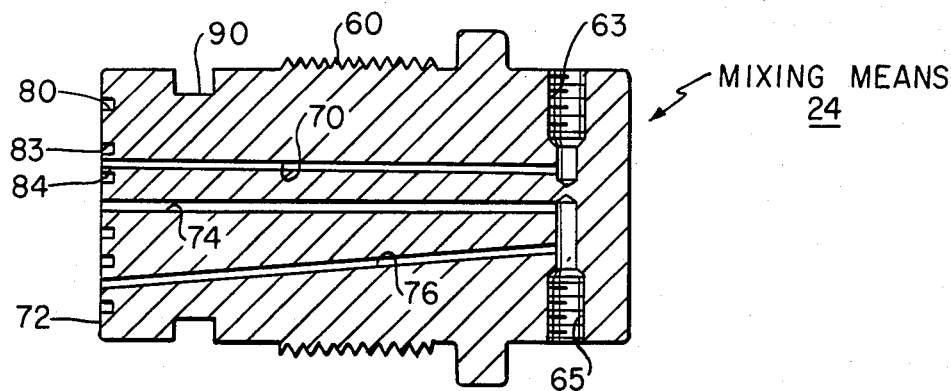
FIGS. 3A and 3B are detailed diagrams of the mixing means shown in FIG. 1.
Figure 3B:
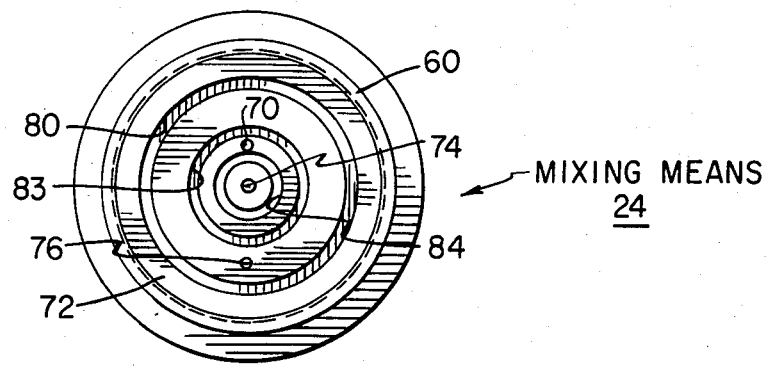

Entrance port 65 is connected to two channels 74 and 76 which conduct fluid entering entrance port 65 to surface 72 of mixing means 24. Also shown on face 72 are grooves 80, 83 and 84 for O-rings. As can be seen in FIG. 3B these grooves are circular in nature. Another groove 90 is for holding an O-ring so as to seal mixing means 24 with test cell 23 when so engaged.

The fluids entering entrance ports 63 and 65 are conducted to surface 72 which is adjacent to end surface of core 25. The fluids immediately start entering test core 25 and combines to form the two phase liquid. Experiments have shown that this manner of liquid mixing has achieved the desired goal of a two phase liquid throughout core 25.

A more detailed construction of test cell 23 is disclosed with the appropriate fittings which are well known to one in the art, in U.S. application Ser. No. 336,136, filed Dec. 31, 1981, assigned to Texaco Inc., assignee of the present invention. Test cell 23 of that construction has been modified to provide for pressure sensors 47 and 48 to be mounted thereon to sense the pressure in core 25. It is preferred that core 25 is obtained from the same earthen formation that contains the petroleum reservoir. With the length of core 25 being 4 inches long and pressure sensors 47 and 48 being 3 inches apart, it is preferred that sensors 47, 48, be located a half inch in from the nearest end. The distance of the half inch eliminates end effects. The distance of 3 inches may also be changed, the main objectives in placement of pressure sensors 47, 48 are to have a substantial length between pressure sensors 47, 48 and to avoid end effects. The aforementioned application does not disdclose mixing means 24.

Computer means 44 basically solves the Darcy's equation set forth as follows.

$$Qo = (K)(Kro)[\Delta pA/\mu oL] \qquad 1.$$

and $$Qw = (k)(Krw)[\Delta pA/\mu wL] \qquad 2.$$

where Qo and Qw are the volume flow rates of the oil and the water respectively, in cm$^3$/sec., K is the absolute permeability of core 24 to single phase liquid flow in darcies, Kro and Krw are the relative permeabilities of core 24 to oil and water, respectively, L is the distance between pressure sensors 47 and 48 in cm, $\Delta p$ is the pressure drop of the fluid along the length L in atm, A is the cross sectional area of core 24 in cm$^2$, and $\mu o$ and $\mu w$ are viscosities of the oil and water, respectively, in cp at test conditions.

The values for Qo and Qw are determined from the following equations $$Qo = f_o Q_T, \qquad 3.$$

and $$Qw = f_w Q_T, \qquad 4.$$

where $Q_T$ is the total volume flow rate of the two phase liquid which may be predetermined by controlling pump means 3 and 3A.

The foregoing relates to the basic method and apparatus for measuring the oil and water relative permeabilities and the water saturation. However, the procedure is more detailed than previously set forth and is as follows. It will be assumed that at the start of each test that core 25 has been cleaned and evacuated. The calibration is as set forth in the aforementioned U.S. application but will be repeated here at the cost of being repetitious. Initially microwave transmitter 36 radiates core 25 in test cell 23 while core 25 has no liquid in it so that a first test value is entered into computer means 44 by receiver means 43. To the microwave equipment it is as if core 25 were filled only with oil and thus this first test value corresponds to an oil filled core reading.

Pump means 3, distilled water source 5, brine source means 8, operate to fill core 25 of test cell 23 with brine. When the brine is observed entering effluent fraction collector 32, a second reading provided by receiver means 33 is entered into computer means 44 and is indicative of the salt water in core 25. In the third calibration step, pump means 3A is operated until only crude oil enters effluent fraction collector 32. A third reading provided by receiver means 43 at this time is representative of residual brine-to-oil injection.

Pump means 3 is again activated to pass brine from brine source means 8 to test cell 23 until only salt water enters effluent fraction collector 32. A fourth measurement at this time corresponds to residual oil-to-waterflood. Further, each time at the end of the third and fourth calibration readings, a conventional material balance is carried out to determine the oil saturation measurements for the conditions of those two steps. That information is also entered into computer means 44. Computer means 44 in effect establishes a calibration curve from the data of the calibration process and determines the water saturation from the received microwave energy and its relation to the curve.

At this point, test cell 23 is removed from the test system and again cleaned by flushing with distilled water, then isopropyl alcohol, then toluene, then isopropyl alcohol, then distilled water and finally flushed with reservoir brine and returned to the test apparatus. Of course it will be obvious to one skilled in the art that distilled water may also be pumped directly into test cell 23 with proper valve control and that the other cleaning fluid may also be used for in-system cleaning of core 25 if so desired.

With test cell 23 back in the test system and ready for testing, a single phase injection mode is initiated. This simply means that the system is operated so that only oil source means 9 is providing oil to test cell 23. Transmitter means 36, receiver means 43 and computer means 44 are then operated to determine the relative permeability $K_{ro}$ of core 24 for oil. The relative permeability $K_{rw}$ of core 25 for water during this step is zero. Computer means 44 does this in accordance with the preprogrammed Darcy's equations 1 and 2 hereinbefore mentioned using the sensed pressure differential $\Delta p$ and the water saturation $S_w$ obtained from the output from receiver means 43 and computer means provides an output to readout means 57 for showing $K_{ro}$ and $S_w$.

The test system is again operated but this time both pump means 3 and 3A are operated in a manner to provide a two phase liquid having 98% crude oil and 2% brine. Again $\Delta p$ and water saturation $S_w$ are measured and the relative permeabilities $K_{ro}$ and $K_{rw}$ for oil and water, respectively, are computed by computer means 44. These operations are repeated for various ratios of brine and crude and are usually done in ascending percentage values of brine. After the step involving 100% brine is reached, all of the steps are then repeated with a descending percentage of brine, starting with 100% brine injection liquid and ending with zero percent brine injection liquid. The reverse order of percentage of brine allows for hysteresis of core 25 in response to the changing of the injection liquid.

The present invention measures the permeability of a core of earthen material using a two phase liquid without the simulation of a two phase liquid.

What is claimed is:

1. A method of determining the oil and water relative permeabilities and the water saturation of a core of earthen material comprising the steps of:
    providing two types of liquid, in a manner so that the two liquids mix to form a two phase liquid which moves through the core,
    controlling the volume flow of each type of liquid so as to control the composition of the two phase liquid,
    irradiating said core with microwave energy with the liquid in the core,
    receiving the microwave energy that has passed through the core,
    determining the water saturation of the core in accordance with the received microwave energy,
    sensing the pressure drop of the liquid along the predetermined length of the core, and
    determining the oil and water relative permeabilities of the core in accordance with properties of the core, the oil fraction of the liquid, the water fraction of the liquid, and the flow rate of the liquid.

2. A method as described in claim 1 in which the determining the relative permeabilities step includes determining the relative permeabilities in accordance with the following equations:

$$Qo=(K)(Kro)[\Delta pA/\mu oL], \qquad 1.$$

$$Ow=(K)(Krw)[\Delta pA/\mu wL], \qquad 2.$$

$$Qo=foQ_T, \qquad 3.$$

and $$Q_w=fwQ_T \qquad 4.$$

where $Q_T$, Qo and Qw are the total volume flow rate of the liquid, the volume flow rate of the oil and the volume flow rate of the water, respectively; K, Kro and Krw are the core's absolute permeability, relative permeability to oil and relative permeability to water, respectively; $\mu o$ and $\mu w$ are the viscosities of the oil and water, respectively; $\Delta p$ is the pressure drop along the predetermined length of the core; A and L are the cross-sectional area of the core and the predetermined length of the core, respectively; and fo and fw are fractional volume flow rates of the oil and the water, respectively.

3. A method as described in claim 2 in which the microwave energy has a frequency within the X-band of microwave frequencies.

4. A method as described in claim 2 in which the microwave energy has a frequency within the K-band of microwave frequencies.

5. Apparatus for determining the oil and water permeabilities and the water saturation of a core of earthen material comprising:
   means for providing two types of liquids;
   a test cell containing a core of earthen material, said test cell including means receiving the two types of liquids for providing a two phase liquid through the core;
   transmitter means for irradiating the test cell with microwave energy;
   receiver means for receiving microwave energy that has passed through the core in the test cell and providing a signal representative thereof; and
   means connected to the pressure drop sensing means and to the receiver means for determining the oil and water relative permeabilities of the core in accordance with the sensed pressure drop and the flow rate of the liquid and for determining the water saturation of the core in accordance with the signal from the receiver means.

6. Apparatus as described in claim 5 in which the relative permeability determining means determines the oil and water permeabilities in accordance with the following equations:

$$Q_o = (K)(K_{ro})[\Delta pA/\mu_o L], \quad 1.$$

$$Q_w = (K)(K_{rw})[\Delta pA/\mu_w L], \quad 2.$$

$$Q_o = f_o Q_T, \quad 3.$$

and $$Q_w = f_w Q_T \quad 4.$$

where $Q_T$, $Q_o$ and $Q_w$ are the total volume flow rate of the liquid, the volume flow rate of the oil and the volume flow rate of the water, respectively; K, Kro and Krw are the core's absolute permeability, relative permeability to oil and relative permeability to water, respectively; $\mu_o$ and $\mu_w$ are the viscosities of the oil and water, respectively; $\Delta p$ is the pressure drop along the predetermined length of the core; A and L are the cross-sectional area of the core and the predetermined length of the core, respectively; and fo and fw are fractional volume flow rates of the oil and the water, respectively.

7. Apparatus as described in claim 5 in which the means for providing the two types of liquids includes:
   a source of brine,
   a source of crude oil,
   pump means connected to the brine source and to the oil source for pumping the brine and the crude oil to the test cell in a predetermined manner.

8. Apparatus as described in claim 5 in which said test cell further includes:
   a shell in which the core is situated, and
   epoxy material maintains the core within the housing; and
   absorber rods located in the epoxy material in such a manner that the microwave absorber rods are situated by diametrically opposite sides of said test cell and test cell is arranged so that the longitudinal axis of the irradiating beam of microwave energy passes between the absorber rods.

9. A monitor as described in claim 8 in which the transmitter means includes microwave source means for providing microwave energy,
   an antenna connected to the source means provides the microwave energy from the source means as the beam of microwave energy, and
   attenuating means connected between the source means and the antenna for controlling the microwave energy provided to the antenna means so as to control the strength of the irradiating beam of microwave energy.

10. Apparatus as described in claim 9 in which the receiver means includes:
    detector means for detecting the beam of microwave energy that has passed through said core and for providing an electrical signal in accordance with the detected microwave energy,
    AC logarithmic voltmeter connected to the detector means and providing a visual display representative of the detected microwave beam in accordance with the electrical signal and providing a corresponding electrical output, and
    printing means connected to said voltmeter for making a printed record of the reading of the voltmeter in accordance with the electrical output.

11. A monitor as described in claim 10 in which the microwave source means includes:
    first voltage means for providing a direct current voltage,
    means for providing an alternating current voltage, and
    a Gunn oscillator connected to both voltage means and to the attenuating means and rendered operational by both voltages to provide microwave energy to the attenuating means.

12. A monitor as described in claim 11 in which the detector means includes:
    an antenna receiving the portion of the beam of microwave energy that has passed through said core and providing a corresponding output, and
    a diode detector connected to the antenna provides the electrical signal in accordance with the received microwave energy.

13. A monitor as described in claim 12 in which the microwave transmitter means is operated so that the microwave energy is within the X-band of microwave frequencies, and the antennas in the transmitter means and in the receiver means are horn antennas.

14. A monitor as described in claim 13 in which transmitter means provides the microwave energy within the K-band of microwave frequencies and the antennas in the transmitter means and the receiver means are dielectric rod antennas.

* * * * *